United States Patent
Riedel

(10) Patent No.: US 9,204,808 B2
(45) Date of Patent: Dec. 8, 2015

(54) DEVICE FOR MONITORING AND/OR IMPROVING THE EFFICIENCY OF PHYSICAL TRAINING

(71) Applicant: Sony Corporation, Tokyo (JP)

(72) Inventor: Matthias Riedel, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 525 days.

(21) Appl. No.: 13/649,447

(22) Filed: Oct. 11, 2012

(65) Prior Publication Data

US 2013/0096396 A1    Apr. 18, 2013

(30) Foreign Application Priority Data

Oct. 14, 2011 (EP) .................................. 11185249

(51) Int. Cl.
| | | |
|---|---|---|
| *A61B 5/145* | (2006.01) | |
| *A61B 5/0205* | (2006.01) | |
| *A61B 5/03* | (2006.01) | |
| *A61B 5/1455* | (2006.01) | |

(Continued)

(52) U.S. Cl.
CPC ............... *A61B 5/0205* (2013.01); *A61B 5/03* (2013.01); *A61B 5/0507* (2013.01); *A61B 5/1455* (2013.01); *A61B 5/14546* (2013.01); *A61B 5/0002* (2013.01); *A61B 5/1075* (2013.01); *A61B 5/443* (2013.01); *A61B 5/486* (2013.01); *A61B 5/742* (2013.01); *A61B 5/7405* (2013.01); *A61B 5/7455* (2013.01)

(58) Field of Classification Search
CPC ...... A61B 5/0205; A61B 5/05; A61B 5/0507; A61B 5/1075; A61B 5/7455; A61B 5/742; A61B 5/7405; A61B 5/14546; A61B 2562/0228; A61B 2562/143; A63B 2220/00; A63B 2220/836
See application file for complete search history.

(56) References Cited

U.S. PATENT DOCUMENTS

2004/0215086 A1* 10/2004 Nelson .......................... 600/504
2005/0021110 A1*  1/2005 Maschke et al. ................ 607/88

(Continued)

OTHER PUBLICATIONS

Nikawa, Y., "Medical and dental diagnosis using millimeter-waves," Microwave Conference Proceedings, 2005. APMC 2005. Asia-Pacific Conference Proceedings, vol. 1, no., pp. 4 pp.,, Dec. 4-7, 2005.*

(Continued)

*Primary Examiner* — William Thomson
*Assistant Examiner* — Nathan J Jenness
(74) *Attorney, Agent, or Firm* — Oblon, McClelland, Maier & Neustadt, L.L.P.

(57) ABSTRACT

A device for monitoring the efficiency of physical training in a human or animal includes a millimeter wave generator that generates millimeter wave radiation and a millimeter wave antenna that emits millimeter waves generated by the millimeter wave generator in a predetermined direction. The device includes a coupling element that couples the millimeter wave antenna to the millimeter wave generator and that transmits the millimeter wave radiation to the millimeter wave antenna. The device also includes a reference element that intermittently receives millimeter wave radiation from the millimeter wave antenna and a detector that detects millimeter wave radiation and produces a first data stream. The device further includes a processing unit that receives the first data stream and generates a signal indicating development of a body lactate level over time and an output device indicating the development of the body lactate level over time, to a user.

21 Claims, 7 Drawing Sheets

(51) Int. Cl.
*A61B 5/05* (2006.01)
*A61B 5/00* (2006.01)
*A61B 5/107* (2006.01)

(56) References Cited

U.S. PATENT DOCUMENTS

2006/0025664 A1* 2/2006 Kim et al. .................. 600/365
2010/0076276 A1* 3/2010 Gilland ...................... 600/301

OTHER PUBLICATIONS

Tuba Yilmaz, Robert Foster and Yang Hao, "Detecting Vital Signs with WearableWireless Sensors" Sensors 2010, 10, 10837-10862.*
Andreas Michael Niess et al., "Evaluation of Stress Response to Interval Training at Low and Moderate Altitudes," Medicine & Science in Sports & Exercise, Copyright 2003 by the American College of Sports Medicine, pp. 263-269.
A. M. Niess et al., "Impact of elevated ambient temperatures on the acute immune response to intensive endurance exercise," Eur J Appl Physiol (2003) 89: 344-351.
Kazuhide Ogino et al., "Ammonia Response to Constant Exercise: Differences to the Lactate Response," Clinical and Experimental Pharmacology and Physiology (2000) 27, 612-617.
Mark J. Patterson, "Variations in Regional Sweat Composition in Normal Human Males," Experimental Physiology (2000) 85.6, 869-875.
W. Ament et al., "Lactate and Ammonia Concentration in Blood and Sweat During Incremental Cycle Ergometer Exercise," Int. J. Sports Med 18 (1997) 35-39.
J. Baldwin et al., "Glycogen Availability Does Not Affect the TCA Cycle or TAN Pools During Prolonged, Fatiguing Exercise," J Appl Physiol 94: 2181-2187, 2003.
Michael J. Buono et al., "The Relationship Between Exercise Intensity and the Sweat Lactate Excretion Rate," J Physiol Sci (2010) 60: 103-107.
Troy D. Chinevere et al., "Effect of Heat Acclimation on Sweat Minerals," Medicine & Science in Sports & Exercise, Copyright 2008 by the American College of Sports Medicine, pp. 886-891.
Shona S. Craig et al., "The Betaine Content of Sweat from Adolescent Females," Craig et al. Journal of the International Society of Sports Nutrition 2010, 7:3.
J. M. Green et al., "Effects of High and Low Blood Lactate Concentrations on Sweat Lactate Response," Int J Sports Med 2000; 21: 556-560.
Nassim Hamouti et al., "Sweat Sodium Concentration During Exercise in the Heat in Aerobically Trained and Untrained Humans," Eur J Appl Physiol pp. 1-9, Published online: Mar. 24, 2011.
Tracy J. Horton et al., "Glucose Kinetics Differ Between Women and Men, During and After Exercise," J Appl Physiol 100: 1883-1894, 2006.
Chien-Tsai Huang et al., "Uric Acid and Urea in Human Sweat," Chinese Journal of Physiology 45(3): 109-115, 2002.
Koji Kitada et al., Effect of Exercise Intensities on Free Fatty Acid Uptake in Whole-Body Organs Measured with $^{123}$I-BMIPP-SPECT, Eur J Appl Physiol (2008) 104: 769-775.
B Knoepfli et al., "Off Seasonal and Pre-Seasonal Assessment of Circulating Energy Sources During Prolonged Running at the Anaerobic Threshold in Competitive Triathletes," Br J Sports Med 2004; 38: 402-407.
Alexander Kratz et al., "Effect of Marathon Running on Hematologic and Biochemical Laboratory Parameters, Including Cardiac Markers," Am J Clin Pathol 2002; 118: 856-863.
Gregory D. Lewis et al., "Metabolic Signatures of Exercise in Human Plasma," Sci Transl Med. May 26, 2010; 2(33) pp. 1-26.
G. Lippi et al., "Acute Variation of Biochemical Markers of Muscle Damage Following a 21-km, Half-Marathon Run?," The Scandinavian Journal of Clinical & Laboratory Investigation, vol. 68, No. 7, Nov. 2008, 667-672.
Fabio Santos Lira et al., "Is Acute Supramaximal Exercise Capable of Modulating Lipoprotein Profile in Healthy Men," Eur J Clin Invest 2010; 40 (8): 759-765.
F. Meyer et al., "Effect of Age and Gender on Sweat Lactate and Ammonia Concentrations During Exercise in the Heat," Brazilian Journal of Medicinal and Biological Research (2007) 40: 135-143.
Kai Roecker et al., "Heart Rate Prescriptions from Performance and Anthropometrical Characteristics," Medicine & Science in Sports & Exercise, Copyright 2002 by the American College of Sports Medicine, pp. 881-887.
K. Roecker et al., "Heart-Rate Recommendations: Transfer Between Running and Cycling Exercise?," Int J Sports Med 2003; 24: 173-178.
Brent C. Ruby et al., "Gender Differences in Glucose Kinetics and Substrate Oxidation During Exercise Near the Lactate Threshold," J Appl Physiol 92: 1125-1132, 2002.
M. P. Schwellnus et al., "Serum Electrolyte Concentrations and Hydration Status are not Associated with Exercise Associated Muscle Cramping (EAMC) in Distance Runners," Br J Sports Med 2004; 38: 488-492.
J. E. Smith et al., "Effects of Prolonged Strenous Exercise (Marathon Running) on Biochemical and Haematological Markers Used in the Investigation of Patients in the Emergency Department," Br J Sports Med 2004; 38: 292-294.
C. G. Stathis et al., "Purine Loss After Repeated Sprint Bouts in Humans," J Appl Physiol 87: 2037:2042, 1999.
S. Zhao et al., "Muscle Adenine Nucleotide Metabolism During and in Recovery from Maximal Exercise in Humans," J Appl Physiol 88: 1513-1519, 2000.
Jacek Zielinski et al., "The Effect of Endurance Training on Changes in Purine Metabolism: A Longitudinal Study of Competitive Long-Distance Runners," Eur J Appl Physiol (2009) 106: 867-876.

* cited by examiner

DEVICE FOR MONITORING AND/OR IMPROVING THE EFFICIENCY OF PHYSICAL TRAINING

FIELD OF INVENTION

The present invention relates to a device for monitoring and/or improving the efficiency of physical training in a human or animal. The present invention in particular deals with a device for non-invasively monitoring body lactate levels in a user and providing training advice based on the development of the body lactate level over time. The present invention furthermore relates to a sensor unit for non-invasively monitoring the body lactate level and to a method for improving physical training in a human or animal.

BACKGROUND OF THE INVENTION

Lactate is a metabolite of the anaerobic metabolism of glucose. During this metabolic process, one molecule of glucose is cleaved into two lactate molecules, whereby energy is obtained for the cell via the production of adenosine triphosphate (ATP). As this process takes place without the use of oxygen, it is referred to as anaerobic metabolism. While the former assumptions that the formation of lactate in the body leads to acidosis and, thereby, after the exercises to muscle aches have been largely disproven, the lactate level and, in particular, the lactate threshold, are still of high interest for the assessment of the physical capabilities of a person.

In connection with the assessment of the performance of a person and the effectiveness of training, one of the values generally looked at is the lactate threshold which is also sometimes referred to as the anaerobic threshold. This designates the exercise intensity at which lactate is formed quicker than it can be broken down, and, therefore, accumulates in the blood stream. Since any training for endurance sports, such as long distance running as well as cycling or swimming, leads to the best results if performed under aerobic conditions, the lactate threshold is a good indicator for deciding on the training intensity for endurance sports. Endurance training is widely used in competitive sports but it is also gaining considerable impact in the prevention and rehabilitation of a number of diseases including coronary heart disease, chronic heart failure, diabetes and cancer.

At the moment, the lactate threshold is measured by taking blood samples from a person during a ramp test, whereby the exercise intensity is progressively increased. The individual aerobic threshold, which is widely used as an anchor point for training recommendation can then be determined from these blood samples. The individual aerobic threshold also reflects the so-called maximal lactate steady state (MLSS), which is defined as the highest blood lactate concentration that can be identified as maintaining a steady-state during a prolonged submaximal constant workload. This technology has got the disadvantage that first of all it involves taking blood samples from a person, which is painful and inconvenient. Furthermore, the analysis of the blood either requires laboratory equipment which, therefore, puts the analysis of the lactate threshold out of reach of most people, or is performed by portable devices like glucose measurement devices which are, however, invasive. The analysis of the blood samples in a laboratory takes time so that this technology is not suitable for monitoring the body lactate levels in normal and, in particular, outdoor training scenarios. The disadvantage of an invasive lactate monitoring during a training session is the necessity to interrupt exercising for capillary blood sampling. A non-invasive continuous lactate measurement approach would be an innovative solution and would allow application of lactate monitoring in a broader community.

U.S. Pat. No. 5,757,002 describes a method as well as an apparatus for measuring lactic acid in an organism. The system described in this document is based on the reflectance and/or absorbance of near infrared light. The device described in this document though is large and cumbersome and is not suitable as a monitoring device in the usual endurance sports training scenarios.

US 2005/0192493 describes what is called a non-invasive blood analyzing measuring system with some self-calibration capability. The radiation used for analysis purposes again is infrared radiation, in particular near infrared radiation, and lactate is mentioned as one of the potential analytes. The device described is designed to be used on the earlobe which, again, is undesirable for use in endurance sports training scenarios, as the motion experienced by the device will significantly impair the ability of generating reliable measurements. Furthermore, in view of the applicant's experiences, so far it seems doubtful whether reliable lactate measurements can at all be achieved with the described device. Furthermore, it needs to be noted that the main focus of this document is measuring blood glucose in order to monitor diabetes patients.

BRIEF SUMMARY OF THE INVENTION

It is an object of the present invention to provide a device for monitoring and/or improving the efficiency of physical training in a human and/or animal that can be used in endurance sports training scenarios, which is both, simple to operate and affordable to both, professional and amateur athletes, and which may be used to advantage in the prevention and rehabilitation of a number of diseases including coronary heart disease, chronic heart failure, diabetes and cancer.

According to one aspect of the present invention, there is provided a device for monitoring and/or improving the efficiency of physical training in a human or animal, comprising:

at least one millimeter wave generator that generates millimeter wave radiation, at least one millimeter wave antenna that emits millimeter waves generated by the millimeter wave generator in a predetermined direction, at least one coupling element that couples the millimeter wave antenna to the millimeter wave generator and that transmits the millimeter wave radiation generated by the millimeter wave generator to the millimeter wave antenna, at least one reference element, whereby the at least one reference element at least intermittently receives millimeter wave radiation from the millimeter wave antenna, at least one detector that detects millimeter wave radiation and produces a first data stream, a processing unit that receives the first data stream from the at least one detector and generates a signal indicating a development of the body lactate level over time, and an output device indicating the development of the body lactate level over time to the user.

According to another aspect of the present invention, there is provided a sensor unit for meassuring the development of the body lactate level over time in a human or animal, comprising:

at least one millimeter wave generator that generates millimeter wave radiation, at least one millimeter wave antenna that emits millimeter waves generated by the millimeter wave generator in a predetermined direction, at least one coupling element that couples the millimeter wave antenna to the millimeter wave generator and that transmits the millimeter wave radiation generated by the millimeter wave generator to the millimeter wave antenna, at least one reference element, whereby the at least one reference element at least intermittently receives millimeter wave radiation from the millimeter wave antenna, at least one detector that detects millimeter wave radiation and produces a first data stream, optionally one or more complementing sensors for sensing skin temperature, pulse, perfusion, sweat, pressure and/or skin thickness and an interface for transmitting the first data stream to a processing unit.

In another aspect of the present invention, there is provided a method for improving physical training in a human or animal, comprising the steps of:

generating millimeter wave radiation, directing millimeter wave radiation to the human or animal body, directing millimeter wave radiation to a reference element in close contact with the human or animal body, measuring millimeter wave radiation reflected and/or transmitted by the human or animal body and by the reference element, calculating the relative development and/or trend of the body lactate level over time from the measured millimeter wave radiation, and providing training advice based on the development of the body lactate level over time.

The present invention is based on the idea that in order to provide support in monitoring physical stress and improving the efficiency of physical training in a human or animal, it is not always necessary to measure absolute lactate levels. It can be sufficient to monitor the development of the body lactate level over time during training and to advise the user (in case of a human, most likely the athlete himself, in case of an animal, the person training the animal) when a body lactate level steady state is reached and to inform the user when an accumulation of the lactate occurs, i.e., when an anaerobic state is reached. In latter case, the user can then reduce the intensity of the exercise in order to keep within an aerobic state.

The monitoring can be done by irradiating body tissue with millimeter waves and then measuring the radiation transmitted or reflected by the body tissue and analyzing the obtained data in order to calculate the development of the body lactate level over time. In order to compensate for changes in the measuring environment, in particular for changes in the body temperature, a reference sample which in use is in close contact with the human body is provided, in order to support the calibrating process. All elements necessary for such device can thereby be easily integrated into one or more units which are both light and robust enough to be useful in the usual sports training scenarios.

The monitoring of the body lactate level according to the present invention can thereby take place either directly by producing and analysing signals based on an interaction of the millimeter wave radiation with the lactate present in human or animal body or via the use of one or more marker substances, which are related to or indicative of the blood lactate level. It is thereby also possible to measure a combination of the blood lactate level and one or more marker substances.

Accordingly the advice according to the invention can be based on the measured blood lactate levels, the measured levels of the one or more marker substances or combinations therefore. In general it will be of little interest to the user on which substances the advice is based on exactly, in particular if the advice consists of simple messages such as increase exercise intensity, decrease exercise intensity or keep the current intensity levels. If further information is preferred it will generally be preferable to communicate any measurements to the user in terms of lactate level, such as "lactate level rising" as the lactate level is a concept that is widely accepted and known as an indicator for the exercise intensity.

One marker substance that is thereby of particular interest is bicarbonate. Bicarbonate forms part of the bloods carbonate buffer that compensates for the changing metabolic conditions in the body in order to ensure that the pH of the blood remains at physiological levels. One such change in the metabolism occurs when lactic acid is formed during exercise as explained above. The lactic acid formed reacts with the bicarbonate to give $CO_2$ and water, whereby the $CO_2$ is then quickly removed by the lungs, i.e. the production of lactate leads to reduction in blood bicarbonate. In intense exercise situations the increased production of lactic acid leads to a notable drop in the blood bicarbonate level, whereby it has been shown that in the situations normally encountered during exercise there is an approximately linear relationship between the increase in blood lactate and the decrease in blood bicarbonate, making the correlation between blood lactate and blood bicarbonate particularly simple and straightforward.

Another advantage of the use of bicarbonate as a marker substance is that the concentration of bicarbonate in the sweat (about 2.5 mmol/l) is roughly one order of a magnitude lower than in the blood (about 24 mmol/l). Furthermore it has been shown that during high intensity exercises the blood bicarbonate level can drop by as much as 15 mmol/l, whereas sweat bicarbonate levels are around 2.5 mmol/l, i.e. again notably lower. Therefore changes in the amount sweat produced as well as the sweat composition will only marginally impact on the accuracy of the measurements.

Associated with the increasing elderly populations, many developed countries have several problems including the burden of medical cost. At the same time, it is vital to initiate strategies for healthy elderly to keep them from illness and extend their healthy years. It has been demonstrated that improving aerobic capacity through regular exercise habits is effective against all these problems. Exercise at lactate threshold (LT) is known to have positive effects on physical function and also on many illnesses, such as high cholesterol, high blood pressure, and diabetes. Thus, the invention can also serve in the prevention and rehabilitation of various diseases.

Preferred embodiments of the proposed devices and methods are defined in the dependent claims.

BRIEF DESCRIPTION OF DRAWINGS

These and other aspects of the present invention will be apparent from and explained in more detail below with reference to the embodiments described hereinafter. In the following drawings

DETAILED DESCRIPTION OF THE INVENTION

Figure 1:
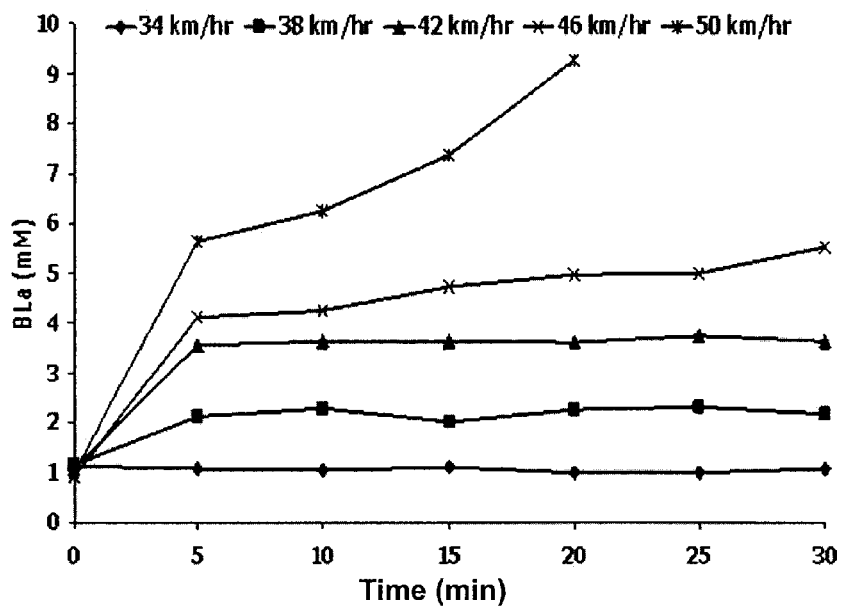
FIG. 1 shows a graph showing the development of the body lactate level over time for five different exercise intensities.

FIG. 1 shows a development of the body lactate level over time for different exercise intensities, the monitoring of which underlies the instant invention. It can be seen from this graph that after about five minutes of an increase of the body lactate level which corresponds to the situation of the body adapting to the new increased energy demand caused by the start of an exercise for cycling speeds of 34 km/h, 38 km/h and 42 km/h, a steady state, i.e. a graph with an average zero slope is attained. This indicates that up to a cycling speed of 42 km/h, the user is in the desired aerobic state during the exercise. At a cycling speed of 46 km/h, an initial steady state is attained which is followed quickly by a slow yet notable increase in body lactate level indicating that the user has gone into an undesired anaerobic state. For the purpose of an efficient training, it would be desirable at this point to reduce the intensity of the exercise to return to the desired aerobic state. The measurements taken at a speed of 50 km/h show a rapid increase of the body lactate level, indicating that the user is operating well beyond the lactate or aerobic threshold.

Figure 2:
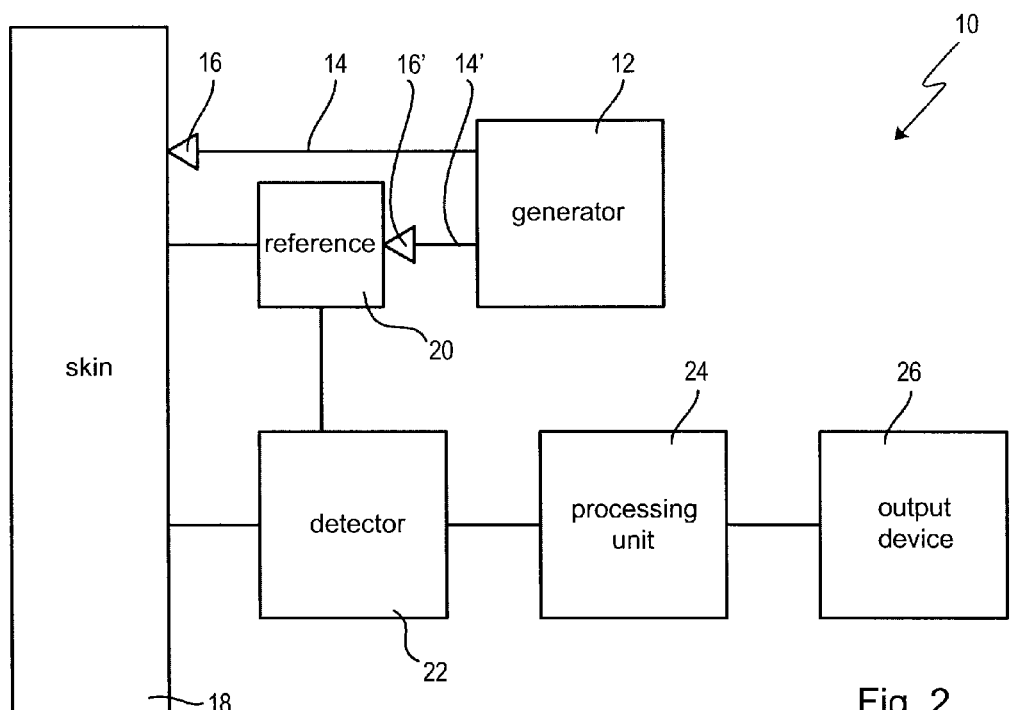
FIG. 2 shows a schematic block diagram of a first embodiment of a device according to the present invention.

FIG. 2 schematically shows an embodiment of a device 10 according to the present invention. This device 10 comprises a millimeter wave generator 12 that generates millimeter wave radiation, as well as coupling elements 14, 14' connecting the millimeter wave generator 12 to corresponding antennas 16, 16'. One of the antennas 16 is thereby arranged such that in use it comes to close or (preferably) real contact with the human or animal body, i.e. the present device is non-invasive in contact with the skin 18. The second antenna 16' is in contact with a reference element 20 which in use is also in direct and close contact with the skin 18 of the user. The reference element 20 can contain any material that is capable of interacting with microwave radiation, examples could be water immobilized into a carrier or physiological saline solutions.

In use, the generator generates millimeter waves which are transmitted through the coupling elements 14, 14' to the antenna 16, 16'. The coupling elements 14, 14' can, thereby, be any coupling element able to transmit the generated millimeter wave radiation of the necessary (efficiently high) frequency. The coupling element 14, 14' may, for example, be implemented e.g. as a waveguide or a high frequency cable.

As an example and as a general guideline, frequencies in the range from 1 to 100 GHz, in particular 10 to 70 GHz, especially in the range of 15 to 35 GHz and preferably around 20 GHz, will usually be used in the present device.

The device 10 further comprises a detector 22 which is arranged such that it can detect millimeter wave radiation transmitted and/or reflected by both the skin and the reference. The detector 22 then generates a data stream based on the millimeter wave radiation detected. This data stream is then transmitted to a processing unit 24 which generates a signal indicating the development of the body lactate level over time which, in turn, is passed on to an output device 26 which indicates the development of a body lactate level over time to the user. The output device 26 can, thereby, be any type of output device suitable for outputting the necessary information. In most cases it will be a visual or an acoustic output device. A visual output device can, for example, display the development (trend) of the lactate level in the form of a graph or via simple traffic light type indicators with, for example, a green light indicating a steady state of the lactate level and a red light indicating an increase in the body lactate level. An acoustic output device can use modulations, for example in the frequency of an emitted sound or in the frequency of intermittent beeps, to indicate a non-steady state in the body lactate level over time, or it could simply output a warning sound when the body lactate level starts to increase or, for more sophisticated embodiments, it could use spoken language. Furthermore, the output device could employ a tactile type of alarm (e.g. a vibration alarm) in order to advise the user.

While it is possible that the sensor and the display are implemented within one unit, in a more likely implementation they will not be within one unit. The sensor (which maybe placed at the upper arm) will preferably transmit its data wirelessly to the display (which may be a watch type device at the wrist).

Preferably, at least the microwave generator 12, the coupling elements 14, 14', the antenna 16, 16' and the detector 22 are combined into one singular unit, for example, on a singular circuit board, in order to produce, for example, together with reference element 20 one integrated sensor unit, whereby such a sensor unit also contains further components which are obvious to a person skilled in the art, such as a power source, for example in the form of a disposable or a rechargeable battery, and necessary connections to connect such a sensor unit to the processing unit and the output device. As mentioned above, it is also possible to combine all components shown in FIG. 2 as well as other necessary components, such as, for example, a power source or input devices, into one self-contained unit, for example to be worn on the wrist of the user.

Figure 3:
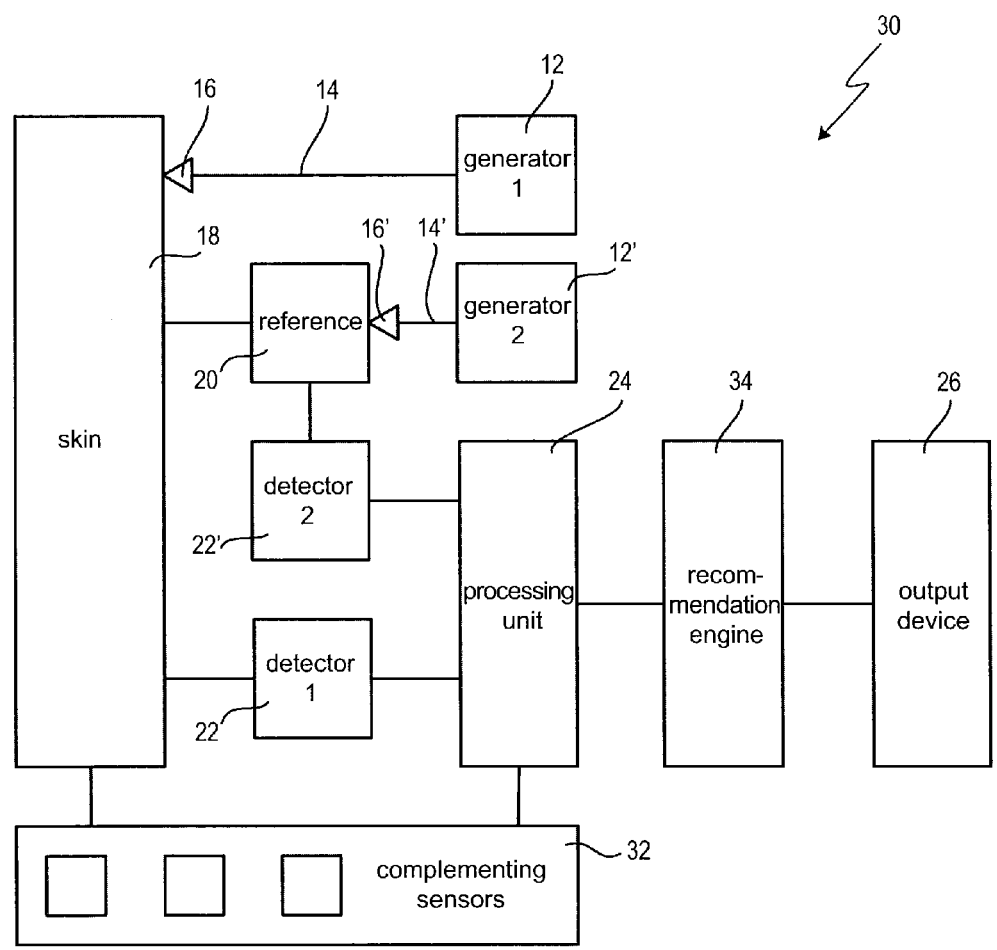
FIG. 3 shows a schematic block diagram of a second embodiment of a device according to the present invention.

FIG. 3 schematically shows a second embodiment of a device 30 according to the present invention. In this figure, as well as in all following figures, those parts of a device according to the present invention which have the same function, are designated with the same reference numerals.

The device 30 differs from device 10 shown in FIG. 2 in that instead of a single millimeter wave generator, the device comprises two millimeter wave generators 12, 12', whereby generator one 12 is connected via a coupling element 14 to antenna 16, which in use of the device is in contact with the skin 18 of the user, and whereby generator two 12' is, via a coupling element 14', connected to antenna 16' which is in contact with reference element 20. The device 30 furthermore comprises two detectors 22, 22', whereby detector one 22 is in contact with the skin 18 of the user and detector two 22' is in contact with the reference element 20. This layout with two generators 12, 12' and two detectors 22, 22' can be advantageous in some situations, as there is no need to switch the generator and/or the detector between the reference and the skin, and, therefore, both areas can be monitored continuously and simultaneously.

Furthermore, the device 30 comprises complementing sensors 32 which, in the present case, comprise a temperature sensor, a pulse sensor, a sweat sensor, a skin thickness sensor, as well as a pressure sensor. Of these sensors, in particular the skin temperature sensor, the sweat sensor and the skin thickness sensor, help to increase the precision of the monitoring of the body lactate level, whereby in particular the occurrence of sweat on the surface of the skin can influence the measurement. The pressure sensor measures how hard the sensors are pushed into the skin, which again can influence the measurement of the body lactate level. The pulse sensor can be used to further monitor the exercise, whereby it can, in particular, be used to ensure that the user is working within an effective, i.e. sufficiently intensive, exercise range. The complementing sensors 32 are also connected to processing unit 24.

The processing unit 24 correlates the data streams produced by the detectors 22, 22' as well as the complementing sensors 32 and generates signals which relate to the development of the body lactate level over time as well as to the physiological data obtained from the complementing sensors 32 and passes those on to recommendation unit 34. This recommendation unit 34 then assesses the signals obtained from the processing unit 24 and compares them to internally stored values such as predetermined lactate profiles based on physiological studies and possibly also to data entered by the user such as gender, age, weight, desired exercise type, desired exercise level etc. and, therefrom, produces recommendations for the user to adapt the training and communicates these recommendations to the output unit 26 which then communicates the recommendations to the user. The recommendation unit thereby in its most sophisticated form will be an expert system providing the user with individually tailored advice on their training. In order to determine when the initial increase of the body lactate level caused by the start of the exercise has finished and a steady state should be reached, the recommendation engine can comprise a timer which provides a waiting cycle between three and ten minutes, preferably around five minutes, before the start of the advice period. Alternatively, the recommendation engine measures the speed of the increase of the body lactate level and, once the initial increase of body lactate level has slowed down, starts the advice period.

Figure 4:
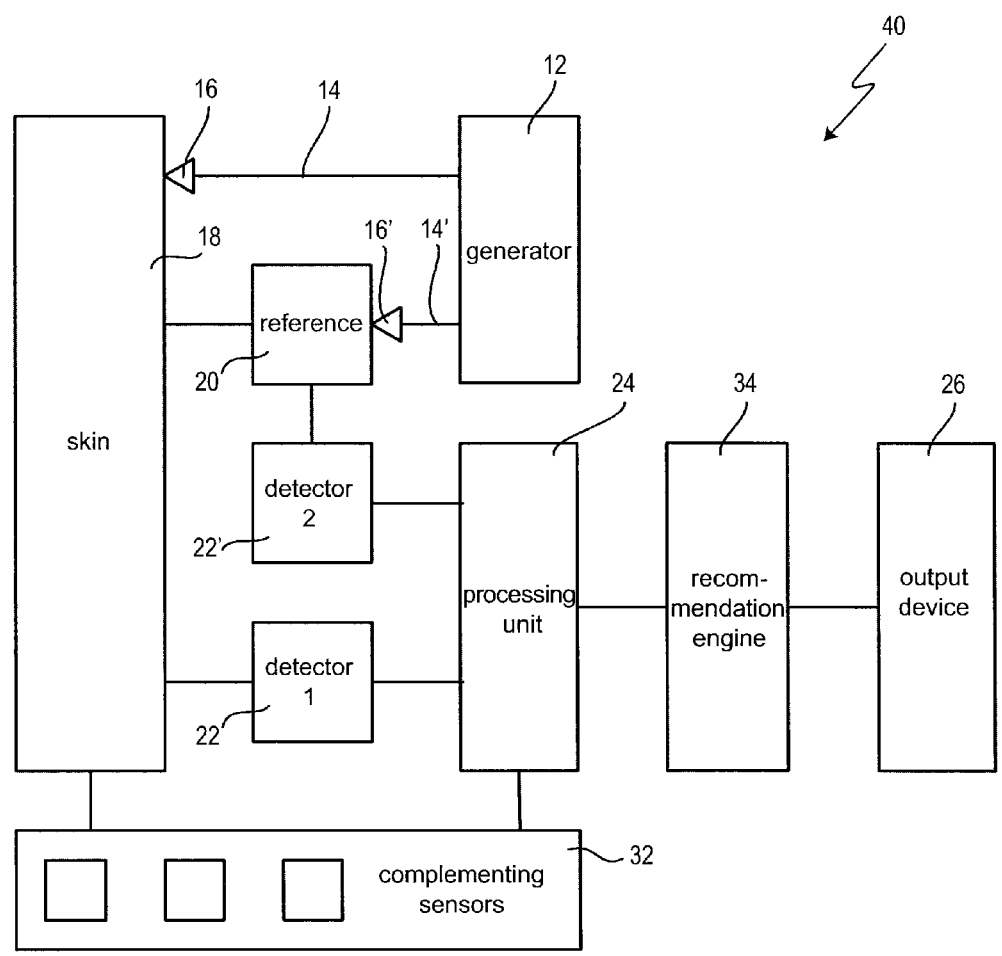
FIG. 4 shows a schematic block diagram of a third embodiment of a device according to the present invention.

FIG. 4 schematically shows a third embodiment of a device 40 of the present invention. This device is quite similar to the device 30 of FIG. 3, the only difference being that here a combination of generator 12 and two detectors 22 and 22' is used to generate and detect the millimeter wave radiation.

Furthermore the device of FIG. 4 is adapted to measure the blood bicarbonate level instead of the blood lactate level. Accordingly the data streams sent to the processing unit 24 relates to the blood bicarbonate level and not the blood lactate level. The processing unit 24 will therefore convert the measured blood bicarbonate levels into the blood lactate levels and communicate this data to the recommendation engine 34, which advises the user based thereon. Alternatively it is also possible for the processing unit 24 to send data relating to the blood bicarbonate level to the recommendation unit 34 and for the recommendation unit 34 to advice the user based on this data.

Alternatively the device can be adapted to also measure the blood lactate level in addition to the blood bicarbonate level. Accordingly the recommendation would then provide advice based on a combination of the two data sets obtained.

Figure 5:
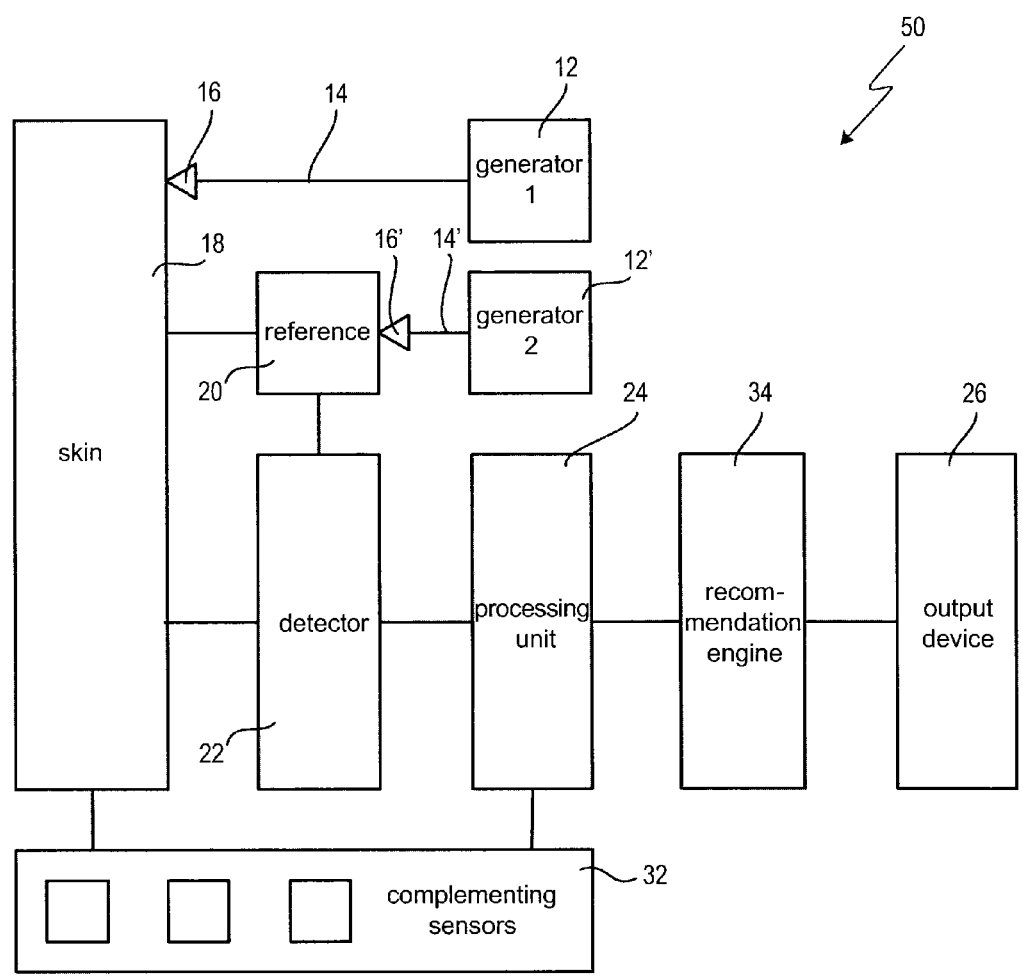
FIG. 5 shows a schematic block diagram of a fourth embodiment of a device according to the present invention.

FIG. 5 schematically shows a fourth embodiment of a device 50 according to the present invention, which again is similar to the device 30 of FIG. 3, the difference being here that two generators 12 and 12' and a singular detector 22 are used instead of the two generators and the two detectors of the device 30.

Figure 6:
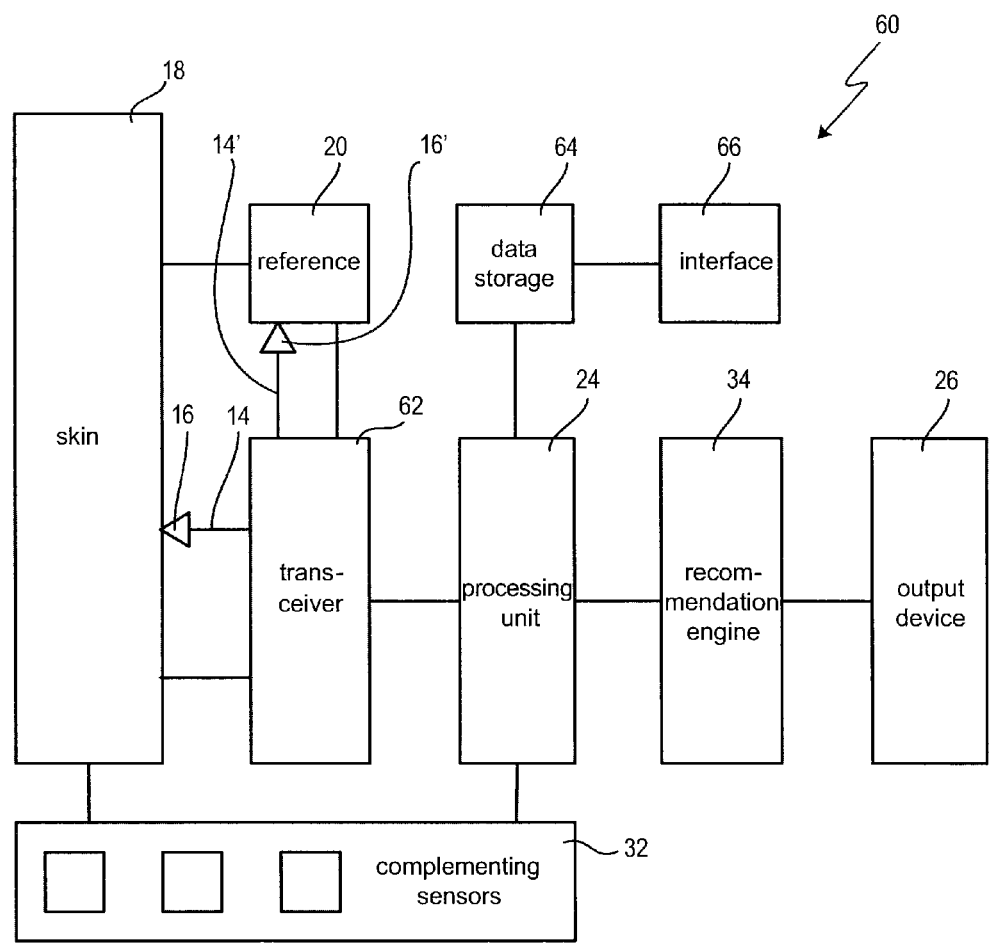
FIG. 6 shows a schematic block diagram of a fifth embodiment of a device according to the present invention.

FIG. 6 schematically shows a fifth embodiment 60 of the present invention. This device differs from device 30 of FIG. 3 in that the generators and the detectors are replaced by a singular transceiver 62 which fulfills the tasks of both the millimeter wave generators and the detectors. Transceiver 62 again is connected via coupling elements 14, 14' to antennas 16, 16' which are in contact with the skin 18 of the user, and the reference element 20. In addition to this, the transceiver 62 is furthermore arranged such, that it can detect millimeter wave radiation transmitted or reflected by the skin 18 of the user and the reference element 20. Based on the millimeter wave radiation detected by the transceiver, again a first data stream is generated and transmitted to processor unit 24. In the instant case, a device comprising a singular transceiver is shown, but it is clear to a person skilled in the art that a solution, for example comprising two or more transceivers, similar to the use of two detectors and two millimeter wave generators in the device 30 of FIG. 3 can also be used.

Furthermore, the device 60 comprises a data storage 64 which is connected to the processing unit 24 and which stores the signals generated by the processing unit 24 based on the first data stream received from the transceiver 62, as well as the data received from the complementing sensors 32 for further analysis once the exercise is finished. In order to transfer the data stored in the data storage 64, the device 60 furthermore comprises an interface 66 which, in the present case, is a simple USB connector which can furthermore also be used to charge an internal rechargeable battery that powers the whole device 60. It is also possible though to use other methods of data transfer for the interface 66 such as a Bluetooth connection, a mobile telephone connection or a mobile data network connection.

Figure 7:
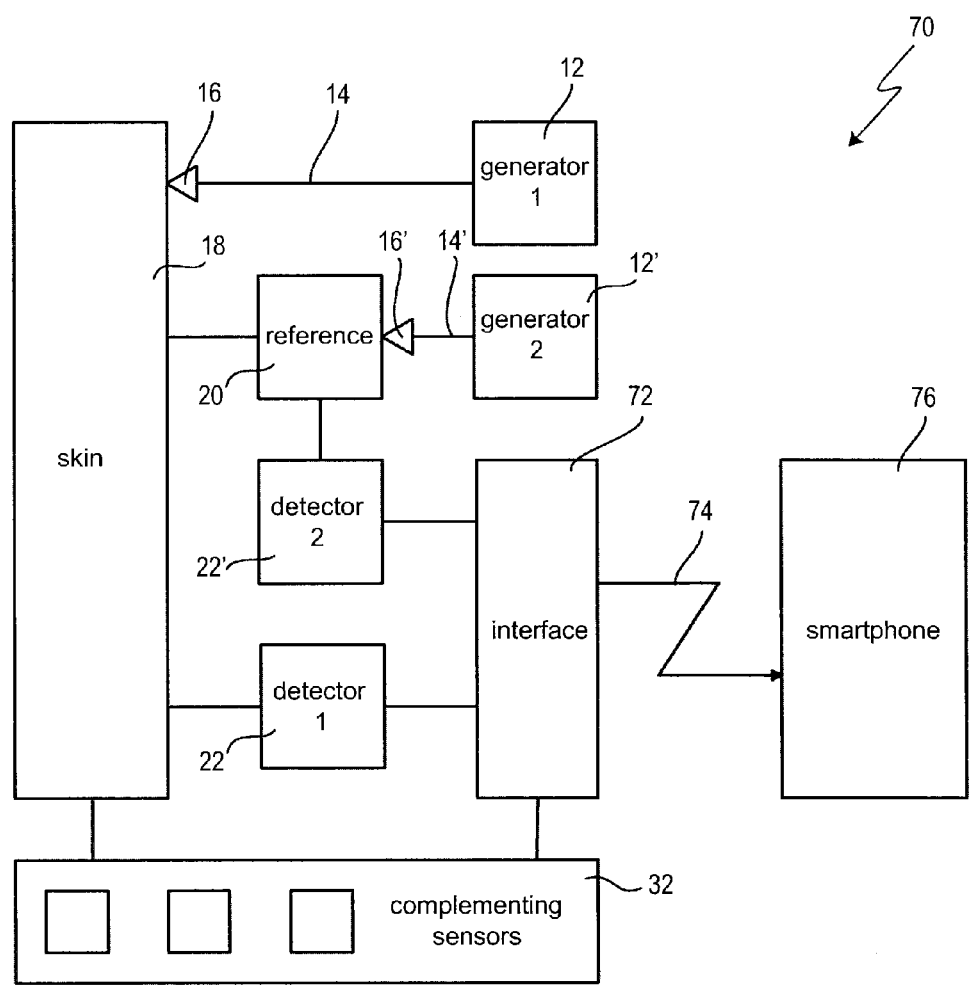
FIG. 7 shows a schematic block diagram of a sixth embodiment of a device according to the present invention.

FIG. 7 schematically shows a sensor unit 70 of the present invention which is connected to a smart phone 76. The sensor unit 70 is, thereby, designed to be a fully enclosed self-contained unit which, in addition to the elements shown here, also comprises all other necessary components such as, for example, a power source. The sensor unit 70 corresponds in large parts to the sensory part of device 30 of FIG. 3, the main difference being here that the processing unit of the device 30 of FIG. 3 has been replaced by an interface 72 which is used to connect the sensor unit 70 to an external computing device which can calculate the development of a body lactate level over time from the data stream generated by the detectors 22, 22'. In the present case, the interface 70 is connected to a smart phone 76 via a Bluetooth connection 74. This setup is particularly suited for use during exercise, whereby the use of a wireless connection enhances the convenience for the user, as there are no wires which might interfere with the physical exercise. The use of a Bluetooth connection is advantageous in this case, as it enables the sensor unit to be connected to a wide range of devices. Nevertheless, it is possible and easily imaginable for a person skilled in the art to use other interface methods, be they wireless or wired, such as, for example, a USB port, which would be useful to connect the unit 70 to a desktop computer, for example in an indoor gym setting, for use in the context of more detailed performance tests.

Figure 8:
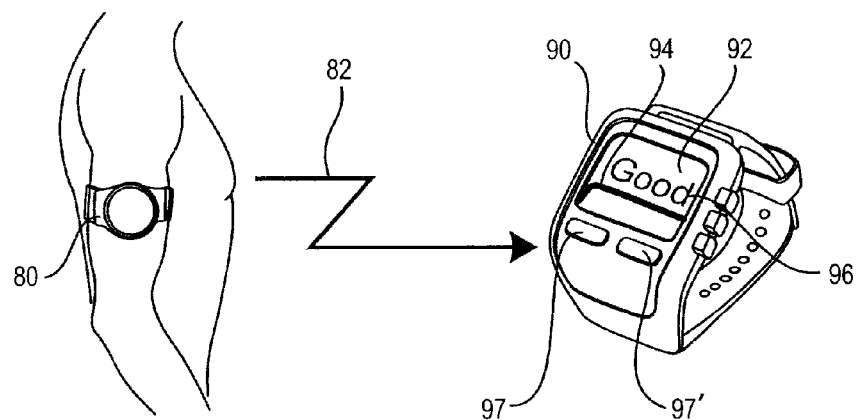
FIG. 8 shows a seventh embodiment of a device according to the invention.

FIG. 8 shows an embodiment of the device of the present invention which consists of a sensor unit 80 which, at the moment, is mounted on the upper arm of a user. This sensor unit 80 contains, for example, all components shown for the sensor unit 70 in FIG. 7. This sensor unit 80 is connected by a wireless connection, in the present case again a Bluetooth connection 82, to a feedback unit 90. This feedback unit 90 contains all other components necessary for a device for monitoring and/or improving the efficiency of physical training in a human or animal, such as, for example, the processing unit 24, the recommendation engine 34 and the output device 26, shown, for example, for the device 30 in FIG. 3. The feedback unit 90 is designed to be worn on the wrist in a similar manner to a wrist watch, as this position makes it easily accessible to the user for most forms of exercise. The output unit 90 comprises a display 92 which in the instant case shows a graph 94 which shows the development of the body lactate level over time as well as messages 92 which indicate whether the exercise intensity is good, too low or too high. Furthermore, the output unit 90 comprises buttons 97, 97' which can be used by the user, for example, to adjust certain parameters in the output unit such as, for example, a minimum pulse frequency, to adapt the training advice to his personal preferences.

Figure 9:
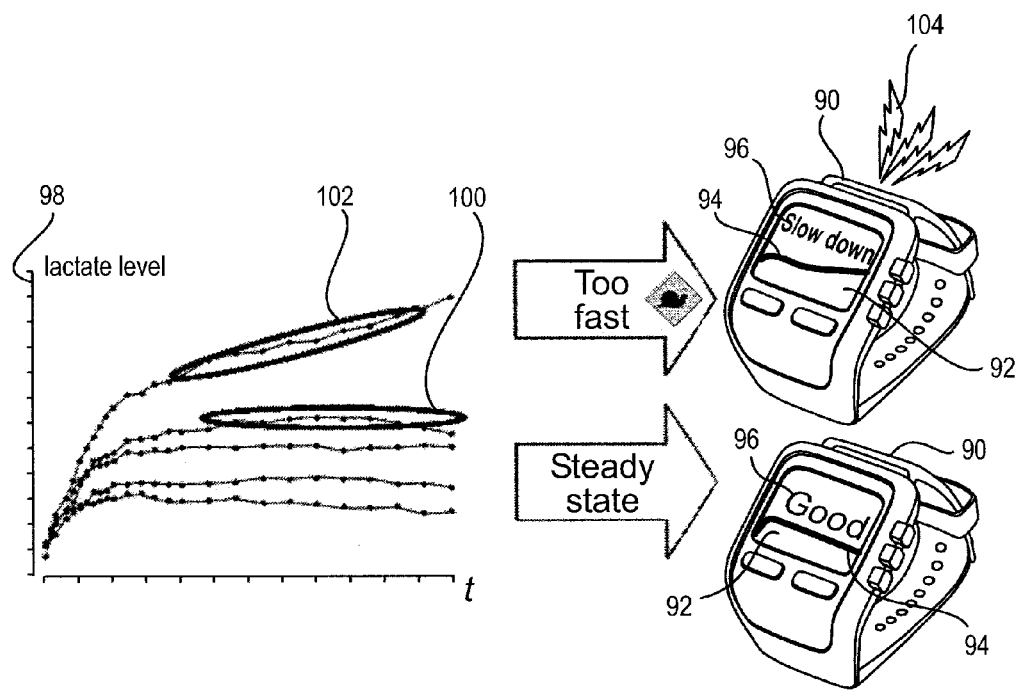
FIG. 9 shows a diagram explaining the working of a method according to the present invention.

FIG. 9 schematically shows a method for improving physical training in a human or animal. Diagram 98 schematically shows the development of the body lactate level over time similar to the graph shown in FIG. 1, again for various strain levels. As can be seen at the beginning of the exercise, the blood lactate level rises sharply in response to the increased energy demand on the body caused by the exercise. Since this rise is perfectly normal and non-problematic, no advice is given to the user at that point in time. Thereby, the period of the normal increasing body lactate level can either be determined by being a simple waiting cycle of usually between three and ten minutes, and mostly around five minutes, as this period of time has been shown to be the normal period of time at which under aerobic conditions a body lactate level steady state is reached. Another possibility is to measure the speed of the increase of the body lactate level over time and start the advisory period once the initial sharp increase in body lactate level has ended.

Designated by reference numeral 100 is an area of the graph in which the steady state for the body lactate level over time has been reached, indicating that the user is exercising in the desired aerobic state. Accordingly, the graph 94 on the display 92 of the output unit 90 shows a straight graph, as well as the word "Good" as a message 96 indicating that the level of exercise is the desired one.

The area marked with reference numeral 102 shows an area of an increasing body lactate level indicating that the user has moved from an aerobic state to an anaerobic state which is undesirable. Correspondingly, the graph 94 of display 92 of the output unit 90 shows a rising graph and the message 96 reads "Slow down", indicating to the user that the exercise intensity should be reduced. In addition to the visual output, the output unit 90 also produces an acoustic signal 104 in the form of warning beeps.

As can be seen underneath the area of steady state 100, there are further graphs which show a steady state at lower exercise intensities. In order to make sure that the user works as close as possible to his lactate threshold, i.e. as close as possible to the anaerobic state, further physiological parameters can be used to avoid underexercise, such as, for example, the pulse, in which case the output unit 90, for example, would then display messages indicating to the user that he is going to slow and that he should increase his exercise intensity. In summary, the device, the unit and the method of the present invention provide a way of monitoring the body lactate level non-invasively without the use of complex and expensive equipment. The devices are easy to use and can greatly enhance the training efficiency for a user, while the known invasive solutions are inconvenient and not applicable while exercising. Further, the present invention does not require the use of (expensive) disposable test strips.

The invention has been illustrated and described in detail in the drawings and foregoing description but such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device for monitoring and/or improving the efficiency of physical training in a human or animal, comprising:
    at least one millimeter wave generator that generates millimeter wave radiation,
    at least one millimeter wave antenna that emits said millimeter waves generated by said millimeter wave generator in a predetermined direction,
    at least one coupling element that couples said at least one millimeter wave antenna to said millimeter wave generator and that transmits said millimeter wave radiation generated by said millimeter wave generator to said at least one millimeter wave antenna,
    at least one reference element that at least intermittently receives a first portion of said millimeter wave radiation from said at least one millimeter wave antenna,
    at least one detector that detects said millimeter wave radiation and produces a first data stream,
    circuitry configured to receive said first data stream from said at least one detector, to calculate from the first data stream a change of a body lactate level over time, to generate a signal indicating the change of the body lactate level over time, and to generate training advice based on the change of the body lactate level over time, and
    an output device indicating said change of said body lactate level over time and said training advice to a user.

2. The device of claim 1,
    further comprising one or more complementing sensors for sensing skin temperature, pulse, perfusion, sweat, pressure and/or skin thickness.

3. The device of claim 1,
    wherein at least one millimeter wave generator, at least one millimeter wave antenna, at least one coupling element, at least one reference element, and at least one detector are combined in one housing to form a sensor unit.

4. The device of claim 3,
    wherein said sensor unit comprises two millimeter wave generators, two millimeter wave antennas, two coupling elements, one reference element, and two detectors.

5. The device of claim 3,
    comprising several sensor units.

6. The device of claim 3, wherein said circuitry and said output device are combined in one housing to form a feedback unit, and,
    wherein said at least one sensor unit and said feedback unit communicate via a wireless data link.

7. The device of claim 1,
    wherein said circuitry and said output device are combined in one housing to form a feedback unit.

8. The device of claim 7,
    wherein said feedback unit is designed to be worn on a wrist of said user.

9. The device of claim 1,
    wherein said output device generates a tactile, visual or acoustic output.

10. The device of claim 9, wherein said output device shows a graph of said change of said body lactate level over time.

11. The device of claim 1, wherein said circuitry is further configured to store data relating to said change of said body lactate level over time.

12. The device of claim 11, further comprising at least one interface for downloading said data relating to said change of said body lactate level over time to an external device.

13. The device of claim 12, wherein said interface is selected from the group consisting of a USB interface, a Bluetooth connection, a mobile telephone connection or a mobile data network connection.

14. The device of claim 1, wherein said circuitry is further configured to time an operation of the device.

15. The device of claim 1, wherein said millimeter wave generator is operable to generate radiation in a range from 1 to 100 GHz.

16. A method for improving physical training in a human or animal, comprising the steps of:
generating millimeter wave radiation,
directing said millimeter wave radiation to a human or animal body,
directing said millimeter wave radiation to a reference element in close contact with said human or animal body,
measuring millimeter wave radiation reflected and or transmitted by said human or animal body and by said reference element,
calculating a relative development and/or trend of a body lactate level over time from said measured millimeter wave radiation, and
providing training advice based on said development of said body lactate level over time.

17. The method of claim 16, further comprising providing a waiting cycle between a start of an exercise and a start of providing the training advice.

18. The method of claim 17, wherein a duration of said waiting cycle is between 3 and 10 minutes.

19. The method of claim 16, wherein said step of providing training advice starts after said body lactate level has stabilized.

20. The method of claim 16, further comprising a step of measuring a pulse of a user, and wherein said training advice is provided based on said relative development and/or trend of said body lactate level over time and said pulse.

21. A method for improving physical training in a human or animal, comprising the steps of:
generating millimeter wave radiation,
directing said millimeter wave radiation to a human or animal body,
directing said millimeter wave radiation to a reference element in close contact with said human or animal body,
measuring millimeter wave radiation reflected and or transmitted by said human or animal body and by said reference element,
calculating a change of a body lactate level over time from said measured millimeter wave radiation, and
providing training advice based on said change of said body lactate level over time.

* * * * *